United States Patent [19]

Moran, Jr.

[11] Patent Number: 5,266,694
[45] Date of Patent: Nov. 30, 1993

[54] NYLON COMPONENT RECLAMATION

[75] Inventor: Edward F. Moran, Jr., Clarksboro, N.J.

[73] Assignee: E. I. du Pont de Nemours and Company, Wilmington, Del.

[21] Appl. No.: 963,224

[22] Filed: Oct. 19, 1992

[51] Int. Cl.⁵ .................. C07C 201/12; C07C 211/12
[52] U.S. Cl. ..................... 540/540; 564/498; 564/511
[58] Field of Search ................ 540/540; 564/498, 511

[56] References Cited

U.S. PATENT DOCUMENTS

| | | | |
|---|---|---|---|
| 3,223,731 | 12/1465 | Craig | 564/498 |
| 3,317,519 | 5/1967 | Lazarus et al. | 260/239.3 |
| 4,605,762 | 8/1286 | Mandoki | 564/498 |
| 4,606,762 | 8/1986 | Sikander et al. | 75/81 |
| 4,804,753 | 2/1989 | Schwarz | 540/450 |

FOREIGN PATENT DOCUMENTS

| | | | |
|---|---|---|---|
| 87101541A | 11/1988 | China | 562/571 |
| 553182 | 12/1956 | Italy | 564/488 |
| 7131541 | 9/1971 | Japan | 540/540 |
| 921667 | 3/1963 | United Kingdom | 562/571 |

Primary Examiner—Robert T. Bond

[57] ABSTRACT

A process is disclosed for simultaneously depolymerizing nylon 6 and nylon 6,6 and reclaiming the monomer values by steam distillation.

5 Claims, No Drawings

NYLON COMPONENT RECLAMATION

BACKGROUND OF THE INVENTION

1. Field of the Invention

This invention relates to a process for simultaneously depolymerizing and reclaiming the component parts of, both, nylon 6 and nylon 6,6. The process includes nylon depolymerization to monomer components in a basic system followed by steam distillation of the monomers.

2. Description of the Prior Art

Nylon 6 has previously been depolymerized in the presence of both, acidic and basic catalysts. Acidic catalysts, particularly phosphoric acid and/or its alkali metal salts, have been preferred because they provide higher depolymerization rates. U.S. Pat. No. 3,182,055, issued May 4, 1965 on the application of Bonfield et al., relates to an improved method of depolymerizing nylon 6 with steam in the presence of phosphoric acid. Depolymerization of nylon 6 using basic catalyst sodium amino caproate was disclosed in Japanese publication 56-4550 dated Jan. 30, 1981.

Nylon 6,6 has previously been depolymerized in the presence of acidic and basic reagents and, to some extent, even water; but not in the presence of basic catalysts. Depolymerization of nylon 6,6 by previous methods has resulted in recovery of hexamethylene diamine and adipic acid, while depolymerization using a basic catalyst in accordance with the present invention yields hexamethylene diamine, cyclopentanone, and carbon dioxide, directly, for uncomplicated recovery.

SUMMARY OF THE INVENTION

The present invention provides a process for depolymerizing a mixture of nylon 6 and nylon 6,6 comprising the steps of establishing a molten polymer system including: (i) up to 75 weight percent nylon 6 and 25-100 weight percent nylon 6,6; and (ii) basic nylon depolymerizing catalyst in an amount of 1-50 weight percent, based on the total weight of the polymer, at a temperature of 250° to 400° C.; conducting steam through the molten polymer system; and condensing the steam to obtain a mixture of water, caprolactam, and hexamethylene diamine.

DETAILED DESCRIPTION OF THE INVENTION

In the presence of an acid catalyst, nylon 6 yields caprolactam but nylon 6,6 yields a large variety of relatively useless or difficult-to-isolate decomposition products including pentyl amine, pentyl nitrile, aminocapronitrile, and butyl amine. Simultaneous depolymerization of a mixture of nylon 6 and nylon 6,6, when conducted using a basic catalyst, results in a yield of both, caprolactam and hexamethylene diamine with little of the other products.

Steam stripping of a combination of nylon 6 and nylon 6,6 was expected to yield the same variety of decomposition products as above-named for nylon 6,6; but, instead, it has been discovered that, so long as a basic depolymerizing catalyst is used, depolymerization and steam stripping of a combination of the two nylons can be conducted simultaneously and in the same vessel to recover essentially all of the monomer value of the nylon 6 (caprolactam) and essentially one-half of the value of the nylon 6,6 (hexamethylene diamine). The cyclopentanone and the carbon dioxide from the nylon 6,6 can, also, be recovered, if desired. Thus, the two nylons can be depolymerized and the monomer values recovered without any need for the initial separation of nylon 6 from nylon 6,6. It is becoming increasingly important to reuse waste polymeric materials. The production of monomers from polymer sources in which the monomers are already available in the proper chemical form reduces the need to convert raw material from petroleum to the monomer form at much greater time and expense.

It is, also, becoming increasingly important to reduce the volume of scrap material, such as nylon carpeting, sent to landfills. By this invention, improving on the reclamation of nylon values, petroleum raw materials can be preserved and the burden on landfills can be lessened. Nylon 6 mill waste is routinely recovered in the form of caprolactam by most nylon 6 producers. The recovery of nylon 6 waste is an important aspect of its production because, in the polymerization step, about 10% of the product consists of water soluble caprolactam monomer and low molecular weight oligomers. Fortunately, nylon 6 is easily depolymerized to caprolactam especially in the presence of phosphoric acid, which is also the preferred polymerization initiator. The depolymerized caprolactam can be steam distilled affording a way to recover otherwise lost raw material.

In the production of nylon 6,6, the polymerization is more efficient and there has not been a need to recover unpolymerized monomer. Nylon 6,6 producers generally treat mill waste, depending on quality, by remelting.

Before the present invention, there was no way to efficiently recycle post consumer nylon waste. Since nylon 6 and 6,6 generally share market applications, consumer products might be either. Therefore, post consumer nylon waste will comprise a mixture of the types. Methods to distinguish between and separate the two types of nylon are expensive and time consuming. Thus, recovery of monomers from mixtures of nylon 6 and 6,6 is useful when recycling used consumer products due to the difficulty and expense of separating the nylons into their individual types.

In accordance with the present invention, there is provided a process for obtaining caprolactam from the nylon 6 portion and hexamethylene diamine from the nylon 6,6 portion of a mixture of the two nylons. The process comprises introducing into a reaction zone unsorted waste nylon and enough alkali metal or alkaline earth hydroxide catalyst to make up the amount of catalyst being withdrawn from the reaction zone in the process of purging non-volatile decomposition products. The process includes continuously introducing high temperature steam into said reaction zone; continuously withdrawing from said reaction zone, steam, polymer degradation products and undecomposed polymer melt; maintaining said reaction zone at a temperature of at least 275° C.; and recovering caprolactam and hexamethylene diamine from the degradation products.

The process of this invention can be used to process either nylon 6 or nylon 6,6 alone or in any combination of the two. The process, thereby, accommodates the variability of feed which would be expected to occur when mixed consumer and industrial nylon waste is being processed. In order to realize the benefits of the invention, the combination of nylons should include at least 25 weight percent nylon 6,6. On the other hand, the melt viscosity and the melting temperature of nylon 6,6 are higher than the viscosity and melting temperature of nylon 6; and it has been found advantageous to use a combination of nylon 6 and nylon 6,6 with at least 25 weight percent nylon 6.

The basic nylon depolymerizing catalyst used in this invention is generally taken from the group consisting of alkali metal hydroxides and alkaline earth metal hydroxides, whether used in the hydroxide form or in some other form which, during the depolymerization, is converted to the hydroxide form.

The above-mentioned basic nylon depolymerizing catalysts are, as stated, useful in polymerizing nylon 6; and, therefore, might be expected to be useful in depolymerization of nylon 6. In the polymerization of nylon 6,6, however, only acidic catalysts have previously been found to be useful. It was completely unexpected that these basic nylon depolymerizing catalysts would be useful in depolymerizing nylon 6,6, also.

DESCRIPTION OF THE PREFERRED EMBODIMENTS

In the examples which follow, the nylon depolymerizations were conducted in a reaction vessel fitted with a heating means, a nitrogen purging means, a stirring means, and a steam distillation means including a steam condensing means. Steam was generated by metered delivery of deoxygenated water in a stainless steel tube through a heated sand bath and into the reaction vessel.

EXAMPLE 1

One hundred grams each of nylon 6 and nylon 6,6 were charged into the reaction vessel, along with 85.6 grams of 6-aminocaproic acid and 26.1 grams of sodium hydroxide. When the temperature of the charge reached 291° C., water flow for steam generation was started at 1.5 ml/minute. The process was run for four hours and, after each hour, 12.7 grams of each of nylon 6 and nylon 6,6 were added to the vessel. The condensate was weighed and analyzed every hour. Caprolactam and hexamethylene diamine were each found in the distillate. Results are summarized in Table 1, below.

While the basic depolymerizing catalyst for this example was sodium 6-aminocaproate, substantially the same results would be expected when sodium hydroxide, alone, is used, as will be shown in Examples 2 and 3, below.

TABLE 1

| Time (hr) | Weight (g) of Distill. Collected | Percent Caprolactam in Distill. | Percent Diamine in Distill. | Average Temperature of Melt (C.) |
|---|---|---|---|---|
| 1 | 95.8 | 3.7 | 2.9 | 261 |
| 2 | 103.0 | 3.6 | 5.1 | 274 |
| 3 | 93.0 | 3.8 | 4.1 | 277 |
| 4 | 92.8 | 3.5 | 2.7 | 278 |

EXAMPLE A (Comparative)

One hundred grams each of nylon 6 and nylon 6,6 were charged into the reaction vessel, along with 41.6 grams of sodium phosphate monobasic and 8.4 grams of 85% phosphoric acid. When the temperature of the charge reached 291° C., water flow for steam generation was started at 1.5 ml/minute. The process was run for five hours and, after each hour, 12.7 grams of each of nylon 6 and nylon 6,6 were added to the vessel. The condensate was weighed and analyzed every hour. Caprolactam was the only depolymerized value found in the distillate. Results are summarized in Table A, below.

TABLE A

| Time (hr) | Weight (g) of Distillate Collected | Percent Caprolactam in Distillate | Average Temperature of Melt (C.) |
|---|---|---|---|
| 1 | 78.3 | 11.1 | 265 |
| 2 | 102.2 | 11.4 | 273 |
| 3 | 99.4 | 9.4 | 274 |
| 4 | 96.9 | 8.2 | 274 |
| 5 | 99.6 | 11.5 | 274 |

EXAMPLE 2

Two hundred grams of nylon 6,6 and 74 grams of nylon 6 were charged into the reaction vessel, along with 26.1 grams of sodium hydroxide. When the temperature of the charge reached 250° C., water flow for steam generation was started at 1.5 ml/minute. After one hour, 115 grams of distillate were collected containing 2.5 weight percent caprolactam and 12.5 weight percent hexamethylene diamine. The average temperature of the melt during this run was 280° C.

EXAMPLE 3

Two hundred grams of nylon 6,6 were charged into the reaction vessel, along with 26.1 grams of sodium hydroxide. When the temperature of the charge reached 260° C., water flow for steam generation was started at 1.5 ml/minute. After one hour, 155 grams of distillate were collected containing 22.3 weight percent hexamethylene diamine. No other depolymerized values were found in the distillate. The average temperature of the melt during this run was 292° C.

I claim:
1. A process for depolymerizing a mixture of nylon 6 and nylon 6,6 comprising the steps of:
   (a) establishing a molten polymer system including: (i) up to 75 percent nylon 6 and 25-100 weight percent nylon 6,6; and (ii) basic nylon depolymerizing catalyst in an amount of 1-50 weight percent, based on the total weight of the polymer, at a temperature of 250° to 400° C.;
   (b) conducting steam through the molten polymer system;
   (c) condensing the steam to obtain a mixture of water, caprolactam, and hexamethylene diamine.

2. The process of claim 1 wherein the basic nylon depolymerizing catalyst is selected from the group consisting of alkali metal hydroxides and alkaline earth metal hydroxide.

3. The process of claim 1 wherein the molten polymer system includes 25-75 weight percent nylon 6 and 25-75 weight percent nylon 6,6.

4. A process for depolymerizing nylon 6,6 comprising the steps of
   (a) establishing a molten polymer system including: (i) nylon 6,6; and (ii) basic nylon depolymerizing catalyst in an amount of 1-50 weight percent, based on the total weight of the polymer, at a temperature of 250° to 400° C.;
   (b) conducting steam through the molten polymer system; and
   (c) condensing the steam to obtain a mixture of water and hexamethylene diamine.

5. The process of claim 4 wherein the basic nylon depolymerizing catalyst is selected from the group consisting of alkali metal hydroxides and alkaline earth metal hydroxide.

* * * * *